United States Patent
Yoskovitz et al.

(10) Patent No.: US 9,835,594 B2
(45) Date of Patent: Dec. 5, 2017

(54) AUTOMATIC MECHANICAL SYSTEM DIAGNOSIS

(71) Applicant: AUGURY SYSTEMS LTD., Haifa (IL)

(72) Inventors: Saar Yoskovitz, Haifa (IL); Gal Shaul, Haifa (IL)

(73) Assignee: AUGURY SYSTEMS LTD., Haifa (IL)

( * ) Notice: Subject to any disclaimer, the term of this patent is extended or adjusted under 35 U.S.C. 154(b) by 662 days.

(21) Appl. No.: 13/657,037

(22) Filed: Oct. 22, 2012

(65) Prior Publication Data

US 2014/0114612 A1 Apr. 24, 2014

(51) Int. Cl.
*G01H 1/00* (2006.01)
*G01H 11/00* (2006.01)
(Continued)

(52) U.S. Cl.
CPC ......... *G01N 29/14* (2013.01); *G01N 29/2481* (2013.01); *G01N 29/46* (2013.01);
(Continued)

(58) Field of Classification Search
CPC ...... G01M 13/028; G01M 15/12; G01M 1/22; G01M 3/24; G01M 11/025; G01N 29/14; G01N 29/12
See application file for complete search history.

(56) References Cited

U.S. PATENT DOCUMENTS

| 3,783,680 A | * | 1/1974 | Mason | .................. G01H 1/003 340/683 |
| 4,885,707 A | | 12/1989 | Nichol | |

(Continued)

FOREIGN PATENT DOCUMENTS

| DE | 19933924 A1 | 11/2000 |
| DE | 102011100611 A1 | 11/2011 |
| GB | 2446035 | 7/2008 |

OTHER PUBLICATIONS

International Search Report and Written Opinion for PCT Application No. PCT/IL2013/050825 dated Jan. 15, 2014.
(Continued)

*Primary Examiner* — John Breene
*Assistant Examiner* — Christine Liao
(74) *Attorney, Agent, or Firm* — Ladas & Parry LLP (57) ABSTRACT

A method for automatic diagnosis of a mechanical system of a group of mechanical systems sharing mechanical characteristics includes obtaining data relating to a vibration. The vibration-related data is acquired by a portable communications device configured to communicate with a remote processor. The processor automatically diagnoses the mechanical system by applying a relationship to the obtained vibration-related data. The relationship is based on sets of vibration-related data previously obtained from the mechanical systems. Each set of vibration-related data relates to vibrations of a mechanical system. The relationship is further based on sets of operation data previously obtained for mechanical systems of the group. Each set of operation data indicates a previous state of operation of a mechanical system. Each of the previous states of operation is associated with at least one of the previously obtained sets of vibration-related data.

15 Claims, 4 Drawing Sheets

(51) Int. Cl.
    *G06F 19/00*     (2011.01)
    *G01N 29/14*     (2006.01)
    *G01N 29/24*     (2006.01)
    *G01N 29/46*     (2006.01)
    *G01H 1/04*     (2006.01)
    *G01H 9/00*     (2006.01)
    *G01M 13/02*     (2006.01)
    *G01M 13/04*     (2006.01)
    *G01H 3/08*     (2006.01)

(52) U.S. Cl.
    CPC ............... *G01H 1/003* (2013.01); *G01H 1/04* (2013.01); *G01H 3/08* (2013.01); *G01H 9/00* (2013.01); *G01M 13/028* (2013.01); *G01M 13/045* (2013.01)

(56) References Cited

U.S. PATENT DOCUMENTS

| | | |
|---|---|---|
| 6,301,514 B1 | 10/2001 | Canada et al. |
| 6,484,109 B1 | 11/2002 | Lofall |
| 6,591,226 B1 | 7/2003 | Hartmann et al. |
| 7,308,322 B1 | 12/2007 | Discenzo et al. |
| 2003/0135349 A1* | 7/2003 | Yoshie ............... G05B 23/0275 702/183 |
| 2005/0049834 A1* | 3/2005 | Bottomfield ....... G05B 23/0229 702/183 |
| 2005/0066730 A1* | 3/2005 | Raichle ........................... 73/579 |
| 2005/0096873 A1* | 5/2005 | Klein .................... G01H 1/006 702/184 |
| 2006/0122810 A1* | 6/2006 | Clarke .................. G01M 15/12 702/185 |
| 2007/0198219 A1* | 8/2007 | Havela ................ G01M 13/045 702/187 |
| 2008/0209274 A1 | 8/2008 | Nicholson et al. |
| 2009/0037206 A1* | 2/2009 | Byrne .................... G06Q 10/06 705/305 |
| 2010/0049343 A1 | 2/2010 | Jaiswal et al. |
| 2010/0114806 A1 | 5/2010 | Harrison et al. |

OTHER PUBLICATIONS

Extended European Search Report dated Aug. 18, 2016; Appln. No. 13848354.0-1554/2909685 PCT/IL2013050825.

Jianping Ma, et al; "Applications of fault detection and diagnois methods in nuclear power plants: A review", Progress in Nuclear Energy, vol. 53, Issue 3, Apr. 2011; pp. 255-266.

Wilfried Reimche, et al; "Basics of Vibration Monitoring for Fault Detection and Process Control", Internet Citation, Jun. 2, 2003, 10 pages.

* cited by examiner

AUTOMATIC MECHANICAL SYSTEM DIAGNOSIS

FIELD OF THE INVENTION

The present invention relates to mechanical systems. More particularly, the present invention relates to automatic diagnosis of a mechanical system.

BACKGROUND OF THE INVENTION

Machines and mechanical systems with moving parts, such as motors, engines, bearings, compressors, or pumps, may generate vibrations. The vibrations may form a recognizable pattern. For example, a pattern may be characterized by a spectral distribution of the vibrations. Vibrations that are generated by mechanical systems typically have components with frequencies in the audible and ultrasonic ranges.

In many cases, a pattern of the vibrations that are generated by the mechanical system is related to a state of operation of the machine. For example, a speed of motion of a moving or rotating part may affect the vibration pattern. Thus, vibrations of a machine may be sensed and analyzed to indicate a state of operation of the machine.

SUMMARY OF THE INVENTION

There is thus provided, in accordance with some embodiments of the present invention, a method for automatic diagnosis of a mechanical system of a group of mechanical systems sharing mechanical characteristics, the method including: obtaining data relating to a vibration of the mechanical system, the vibration-related data being acquired by a portable communications device configured to communicate with a remote processing unit; and operating the remote processing unit to automatically diagnose the mechanical system by applying a relationship to the obtained vibration-related data, the relationship being based on a plurality of sets of vibration-related data previously obtained from mechanical systems of the group of mechanical systems, each set of vibration-related data relating to vibrations of a mechanical system of the group of mechanical systems, the relationship being further based on a plurality of sets of operation data previously obtained for mechanical systems of the group of mechanical systems, each set of operation data indicating a previous state of operation of a mechanical system of the group of mechanical systems, each of the previous states of operation being associated with at least one of the previously obtained sets of vibration-related data.

Furthermore, in accordance with some embodiments of the present invention, the mechanical systems of the group of mechanical systems include the mechanical system being diagnosed.

Furthermore, in accordance with some embodiments of the present invention, a set of the previously obtained sets of vibration-related data relates to a vibration that was measured by one or more remote portable communications devices.

Furthermore, in accordance with some embodiments of the present invention, the vibration-related data includes a spectrum of the measured vibration.

Furthermore, in accordance with some embodiments of the present invention, obtaining the vibration-related data includes transmitting the vibration-related data from the portable communications device to the remote processing unit.

Furthermore, in accordance with some embodiments of the present invention, the portable communications device includes a device selected from a list of devices consisting of a mobile phone, a smartphone, and a portable computer.

Furthermore, in accordance with some embodiments of the present invention, the portable communications device is configured to measure a vibration when a vibration sensor is connected to the portable communications device.

Furthermore, in accordance with some embodiments of the present invention, diagnosing the mechanical system includes indicating a current state of operation of the mechanical system.

Furthermore, in accordance with some embodiments of the present invention, diagnosing the mechanical system includes indicating a prediction of future performance of the mechanical system.

Furthermore, in accordance with some embodiments of the present invention, diagnosing the mechanical system includes recommending performance of a maintenance operation on the mechanical system.

Furthermore, in accordance with some embodiments of the present invention, applying the relationship includes selecting an entry in a lookup table.

Furthermore, in accordance with some embodiments of the present invention, the method further includes obtaining data that identifies the mechanical system.

Furthermore, in accordance with some embodiments of the present invention, the method further includes operating in a training mode, operation in the training mode including: obtaining the plurality of sets of vibration-related data; obtaining the plurality of sets of operation data; and analyzing the plurality of sets of vibration-related data and plurality of sets of operation data to generate the relationship.

Furthermore, in accordance with some embodiments of the present invention, the operation data indicates a repair or maintenance operation that was performed.

Furthermore, in accordance with some embodiments of the present invention, the previously obtained set of vibration-related data indicates a vibration of the mechanical system or of the similar mechanical system during a period of time that precedes the previous state of operation that is indicated by the associated previously obtained set of operation data.

Furthermore, in accordance with some embodiments of the present invention, the vibration-related data indicates an ultrasonic acoustic vibration of the mechanical system or a low acoustic frequency vibration of the mechanical system.

Furthermore, in accordance with some embodiments of the present invention, the method further includes obtaining additional sensed data that indicates a property of the mechanical system in addition to a vibration of the mechanical system.

Furthermore, in accordance with some embodiments of the present invention, the indicated property includes a temperature of the mechanical system.

Furthermore, in accordance with some embodiments of the present invention, diagnosing the mechanical system further includes applying the relationship to the additional sensed data, the relationship being further based on one or more previously obtained sets of additional sensed data, each set of additional sensed data indicating the indicated property of the mechanical system or of a similar mechanical system as previously measured by one or more remote portable communications devices.

There is further provided, in accordance with some embodiments of the present invention, non-transitory computer readable medium for automatic diagnosis of a mechanical system of a group of mechanical systems sharing mechanical characteristics, having stored upon instructions that when executed cause the computer to perform the method to: automatically diagnosing the mechanical system by applying a relationship to obtained data relating to a vibration of the mechanical system, the vibration-related data being acquired by a portable communications device configured to communicate with the computer, the relationship being based on a plurality of sets of vibration-related data previously obtained from mechanical systems of the group of mechanical systems, each set of vibration-related data relating to vibrations of a mechanical system of the group of mechanical systems, the relationship being further based on a plurality of sets of operation data previously obtained for mechanical systems of the group of mechanical systems, each set of operation data indicating a previous state of operation of a mechanical system of the group of mechanical systems, each of the previous states of operation being associated with at least one of the previously obtained sets of vibration-related data.

Furthermore, in accordance with some embodiments of the present invention, the medium further includes instructions that when executed cause the computer to perform the method to obtain the plurality of sets of vibration-related data; obtain the plurality of sets of operation data; and analyze the sets of vibration-related data and the sets of operation data to generate the relationship.

Furthermore, in accordance with some embodiments of the present invention, the diagnosis includes an indication of a current state of operation of the mechanical system, an indication of a predicted future performance of the mechanical system, or a recommended maintenance operation to be performed on the mechanical system.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF THE INVENTION

In accordance with embodiments of the present invention, a portable communications device may be utilized to perform automatic diagnosis of a mechanical system. The portable communications device may be operated to sense vibrations or other properties (e.g. temperature) of the mechanical system. Vibration-related data, e.g. in the form of a representation of the sensed vibrations or of a result of an analysis of the sensed vibrations, may be communicated to a remote processing unit or processor. Other sensed properties or characteristics of the mechanical system may similarly be communicated to the remote processing unit.

The remote processing unit, referred to herein as a server, may analyze the vibration-related data. The analysis may include application of a previously determined relationship between vibration-related data and states of operation of mechanical systems of a group of mechanical systems. The group of mechanical systems includes mechanical systems that are similar to, and may include, the mechanical system being diagnosed. The mechanical systems of the group may be characterized by one or more shared characteristics. For example, shared characteristics may refer to type, model number, manufacturer, physical characteristics or dimensions, operating characteristics or parameters, or other shared characteristics that indicate that an observed behavior of one of the mechanical systems of the group may be typical of another mechanical system of the group.

The relationship is based on previous vibration-related data that indicated a previously measured vibration of the mechanical system or of a similar (e.g. same type or model) mechanical system that had been previously communicated to the server. The previously communicated vibration-related data may have been communicated to the server by one or more portable communications devices. Previously communicated operation data that indicates a previous state of operation of the mechanical system may be associated with (e.g. occurred following, or concurrently with) the previously measured vibration. Analysis of the previously communicated vibration-related and operation data may yield the relationship.

A result of the analysis of the communicated vibration-related data may be communicated by the server to the portable communications device. The communicated result may include a diagnosis of the mechanical system. For example, a diagnosis may include specification of a problem, an indication of recommended maintenance activities to be performed, or a prediction of a time to failure (e.g. in the absence of any further maintenance activity). Any indication of a current or predicted future status (prognosis) of the mechanical system, or of an action to be performed, is herein referred to as a diagnosis.

The portable communications device includes communications capability. The portable communications device may include processing capability, for example, in the form of an incorporated processor. For example, the portable communications device may include a portable telephone, smartphone, or computer. Thus, the portable communications device may be an all-purpose device that is not dedicated to vibration sensing or analysis.

The portable communications device may include a wireless sensor. A wireless sensor may include a communications capability (e.g. that includes a network chip, port, or antenna that enables communication with a network) that enables the wireless sensor to communicate with a server or other device via a network. A wireless sensor may include a processing capability (e.g. that includes a processor or computing chip). A wireless sensor may include a data storage capability, e.g. for storing programmed instructions or sensed data.

The portable communications device is configurable to sense vibrations. For example, a vibration sensor may be connected to an appropriate port of connector of the portable communications device. A sensing end of the vibration sensor may be placed in contact with, or in the vicinity of, one or more components of the mechanical system. As another example, a built-in microphone or other sensor of the portable communications device may be utilized to detect audible or ultrasonic vibrations of the mechanical system.

As used herein, a sensed vibration may include any low frequency or high frequency (e.g. ultrasonic) vibration of the mechanical system. (Typically, a low frequency vibration may be indicative of a local condition of the mechanical system, whereas a high frequency vibration may be more indicative of a system-wide condition.)

The vibration sensor may produce an analog electrical signal that corresponds to sensed vibrations. The vibration sensor may include an amplifier or filter, or other analog component, for processing a sensed analog vibration signal. For example, an analog filter may eliminate or reduce signal components whose frequencies are outside a particular range of vibration frequencies (e.g. to eliminate or reduce noise or irrelevant signal frequencies). An amplifier may amplify a weak analog signal so as to enable further processing.

An analog vibration signal (e.g. after amplification and filtering) may be digitized. For example, the vibration sensor may include an analog-to-digital converter. As another example, an analog-to-digital converter of the portable communications device (e.g. of a microphone of the portable communications device) may be utilized to digitize an analog vibration signal. The output of the analog-to-digital converter is a digital signal that corresponds to the analog vibration signal.

The vibration sensor may include a processor, e.g. in the form of a micro-controller. The processor of the vibration sensor may be configured to operate in accordance with programmed instructions. For example, the programmed instructions may be stored in a nonvolatile data storage device that is included in the vibration sensor and that is in communication with the processor of the vibration sensor. The processor of the vibration sensor may be configured to transmit a digital signal to the portable communications device. In accordance with some embodiments of the present invention, processing capability of the portable communications device may be utilized.

The portable communications device includes a processing capability. Thus, the portable communications device may be configured to process a signal that is received from the vibration sensor or from another sensor. Alternatively, a received signal may be transmitted or communicated to a server for processing.

A processing capability of the portable communications device may be configured (e.g. in accordance with a downloaded application or other stored programmed instructions) to apply a signal processing operation to a received digital signal. For example, signal processing operations may include a digital filtering operation, data compression, or a transform operation (e.g. a Fourier transform, e.g. utilizing a fast Fourier transform (FFT) operation) or otherwise extracting one or more characteristics of the digital signal. In particular, extracted characteristics may be interpretable to characterize relevant features of sensed vibrations. The processing may be performed concurrently with receiving the signal (real-time processing).

The characteristics of the digital signal may be communicated to the server, or the digital signal itself (or a compressed form of the digital signal) may be communicated to the server. Communicating a limited number of characteristics to the server may enable more efficient (e.g. faster or reduced bandwidth) communication of vibration features from the portable communications device to the server than communicating the digital signal itself.

Prior to, concurrent with, or subsequent to acquiring and communicating vibration-related data, the portable communications device may be configured to receive data for characterizing the mechanical system that generated the sensed vibrations. The portable may be configured to receive data from other sensors, such as a temperature sensor. For example, the portable communications device may be configured to communicate with a processor or other component of the mechanical system that is configured to generate characterizing data. As another example, the portable communications device may be configured to enable a user to input relevant data. For example, an application that is running on a processor of the portable communications device may cause a user interface to be displayed on a display screen, or otherwise be communicated to the user. The user may utilize one or more input devices (e.g. keyboard, keypad, pointing device, touch-screen, microphone, or camera, near field communication (NFC) tag or radiofrequency identification (RFID) reader) of the portable communications device to input relevant data. Relevant data may include, for example, type of mechanical system, location on or in the mechanical system where the vibration sensor was placed, operating conditions of the mechanical system, environmental factors, or other relevant information.

The server is configured to receive and to analyze or process vibration-related data from one or more portable communications devices. The server may operate in a learning mode or in a diagnosis mode.

When operating in learning mode, the server may analyze vibration-related data from a plurality of vibration measurements, together with additional data. The analysis may result in generation of a correlation between one or more features of the measured vibration and one or more states of operation of the mechanical system. A generated correlation may relate to a type of mechanical system, to a particular component of a mechanical system, or to a particular model of the mechanical system or of the component. When operating in a learning mode, received vibration-related data as well as related data (e.g. that define the mechanical system or its components, or that define a state of operation of the mechanical system or of a component of the mechanical system) may be stored. Correlations may be sought between one or more states of operation and one or more features of the associated vibrations. A confidence of a correlation may be calculated as vibration-related data is accumulated and analyzed. The confidence may typically be expected to increase as additional data is accumulated and analyzed.

When operating in a diagnosis mode, the server may analyze received vibration-related data and other sensed data in light of a previously (e.g. during operation in a learning mode) generated correlation. The analysis may yield a state of operation of the mechanical device. The server may communicate a report of the resulting state of operation to the portable communications device from which the analyzed vibration-related data was received. The communication may include a report of an indication of a level of confidence. The level of confidence may be related to the likelihood that the reported state of operation is correct. For example, the confidence may be indicated to be high if a large amount of vibration-related data had been previously analyzed and lower if only a small amount of data had been analyzed. The state of operation (and the reported level of confidence) may be utilized in selecting a maintenance operation that is to be performed with regard to the mechanical system.

Automatic mechanical system diagnosis, in accordance with embodiments of the present invention, may enable predictive maintenance of a mechanical system, or nondestructive testing of the mechanical system. Automatic mechanical system diagnosis in accordance with embodiments of the present invention may enable vibration sensing and analysis without investing in specialized vibration sensors or analyzers. A user that has access to a portable communications device (e.g. smartphone or portable computer) need only obtain or purchase an acoustic probe that communicates with the portable communications device, and suitable software or a suitable application for enabling treatment of acquired vibration-related data. In accordance with embodiments of the present invention, user need not have specialized knowledge that relates sensed vibrations with a state of the mechanical system in order to perform automatic diagnosis of the mechanical system. Diagnostic information that is returned by the server includes an indication of a problem with the mechanical system, or an indication of a recommended action (e.g. related to maintenance or to preventive repairs or adjustments) to be performed.

Figure 1:
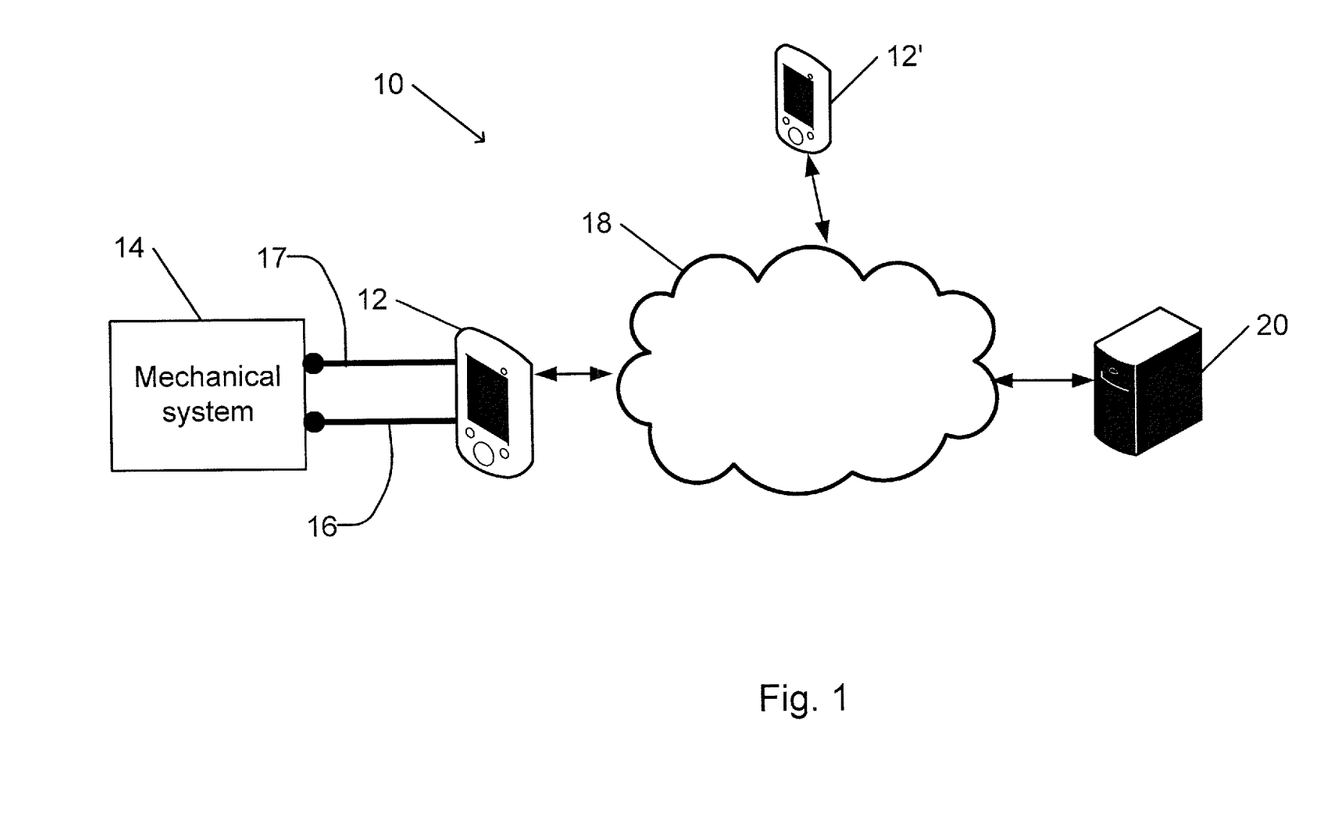
FIG. 1 is a schematic diagram of a system for automatic mechanical system diagnosis, in accordance with an embodiment of the present invention.

A system may be configured to perform automatic mechanical system diagnosis in accordance with embodiments of the present invention. FIG. 1 is a schematic diagram of a system for automatic mechanical system diagnosis, in accordance with an embodiment of the present invention.

Automatic mechanical system diagnosis system 10 includes a server 20 that is configured to communicate with one or more portable communications devices 12 or 12' via network 18.

Network 18 may include a wired or wireless communications network that enables communications between at least, a server 20 and portable communications devices 12 or 12'. For example, network 18 may represent a cellular or other telephone network, the Internet, an intranet, or similar communications network. As used herein, network 18 may be understood as including a direct (wired or wireless) communications channel between server 20 and one or more portable communications devices 12 or 12'.

Figure 2:
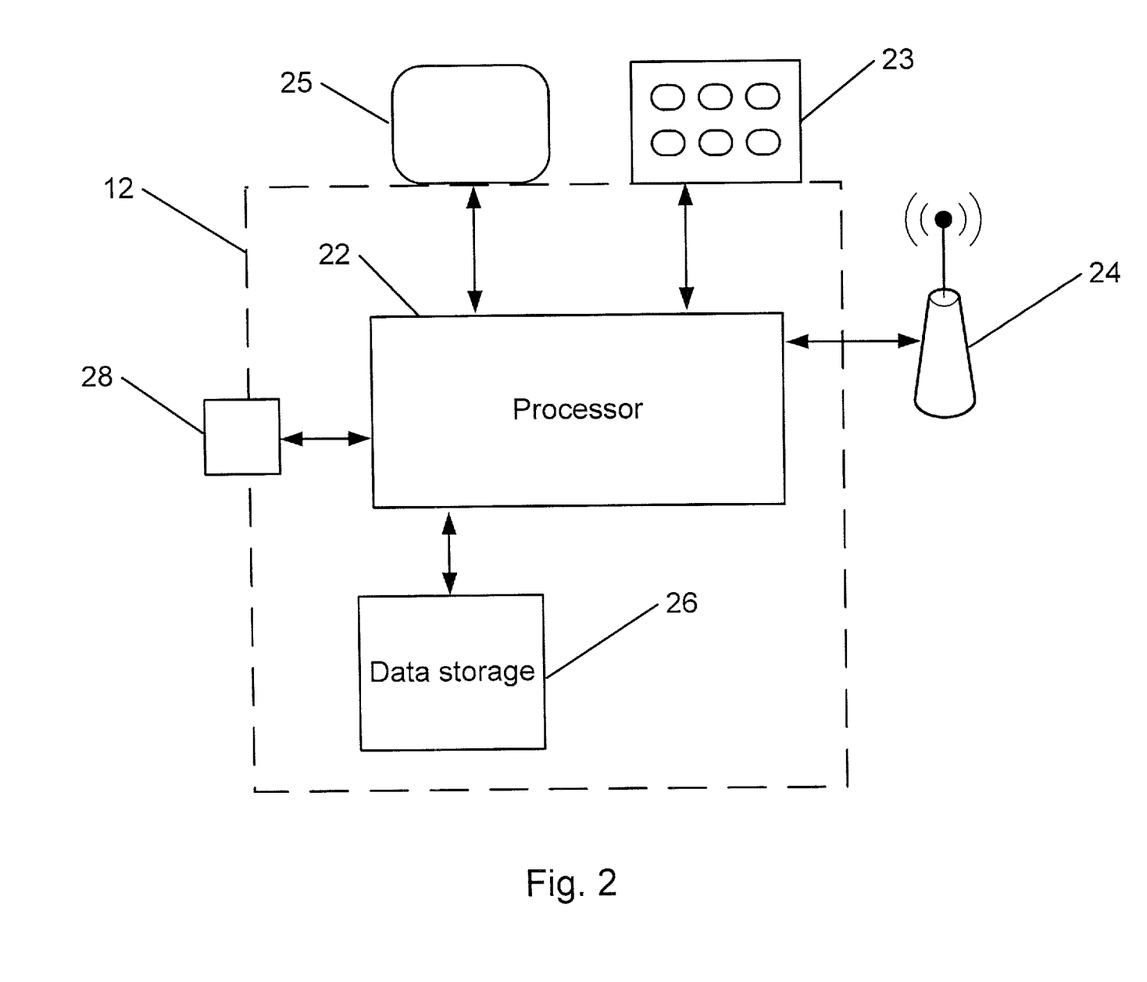
FIG. 2 is a schematic diagram of a server of a portable communications device for automatic mechanical system diagnosis, in accordance with an embodiment of the present invention.

Portable communications device 12 is configured to receive vibration-related signals from acoustic vibration sensor 16 or from additional sensors 17 and to convey sensed vibration-related or other data to server 20 via network 18. FIG. 2 is a schematic diagram of a server of a portable communications device for automatic mechanical system diagnosis, in accordance with an embodiment of the present invention. Portable communications device 12 may include a mobile phone, a smartphone, a portable computer, a vehicle-mounted computer, or another portable device that may be configured to communicate with a server 20. Portable communications device 12 may include processing capability, represented by processor 22. Portable communications device 12 may include volatile or non-volatile data storage capability, represented by data storage unit 26. Processor 22 of portable communications device 12 may be configured to operate in accordance with programmed instructions that are stored on data storage unit 26.

Processor 22 of portable communications device 12 may communicate with network 18 via communications link 24. Communications link 24 may represent a wired or wireless communications link that is suitable for communication with network 18.

Processor 22 is provided with one or more ports or connectors, represented by connector 28. Connector 28 may include a data connection, a power connection, or both. Connector 28 may include a wireless connection (e.g. optical or electromagnetic). A data connection of connector 28 may, for example, enable processor 22 to send control instructions or commands to, or receive data from (or both), an attached sensor or other device. For example, processor 22 may communicate with an acoustic vibration sensor 16 via connector 28.

Instructions may be input to processor 22 by a user of portable communications device 12 by operating input device 23. For example, input device 23 may include one or more of a keyboard, keypad, pointing device, camera, or microphone for enabling a user to input data or instructions for operation of processor 12. Input device 23 may be operated, for example, to indicate when to operate acoustic vibration sensor 16 or additional sensors 17 to sense vibrations of mechanical system 14. Input device 23 may be operated to specify one or more identifying or other characteristics of mechanical system 14. For example, characteristics of the mechanical system may be manually input using a keyboard, keypad, pointing device, or similar user-manipulable device for entering alphanumeric data. As another example, characteristics of the mechanical system may be read from an appropriate tag or device using an NFC or RFID reader.

Mechanical system 14 may include a machine, vehicle, or component of a machine or vehicle. For example, mechanical system 14 may include a motor, engine, bearing, compressor, pump, pipe or conduit, gear or transmission, rotor, wheel, furnace, valve, piston, building, or any other device or component that may generate acoustic vibrations during proper or improper operation.

Processor 22 may communicate with output device 25. For example, output device 25 may include a display screen, printer, display panel, speaker, or another device capable of producing visible, audible, or tactile output. Processor 22 may communicate with an output device 25 to present a result of diagnosis of mechanical system 14.

Acoustic vibration sensor 16 may be operated to sense acoustic vibrations (e.g. audible or ultrasonic frequencies) of mechanical system 14. For example, acoustic vibration sensor 16 may be electrically or wirelessly connected to processor 22, e.g. via connector 28. Acoustic vibration sensor 16 includes a component that generates an electrical signal when exposed to at least some mechanical vibrations. One or more probes of acoustic vibration sensor 16 may be placed in contact with mechanical system 14, or may be placed in the vicinity of mechanical system 14. A probe of acoustic vibration sensor 16 may include, for example, a microphone (e.g. that includes a piezoelectric capacitive component), an optical or electromagnetic vibration sensor, an electromechanical vibration-sensitive device, or similar device that may generate an electric current when exposed to vibrations. Acoustic vibration sensor 16 may include a micro-electromechanical system (MEMS) sensor.

Various probes or other components of acoustic vibration sensor 16 may be sensitive to different types (e.g. frequency, amplitude, or waveform) of vibrations. For example, one probe of acoustic vibration sensor 16 may be sensitive to ultrasonic emissions. Another probe of acoustic vibration sensor 16 may be sensitive to low acoustic frequency vibrations. The various probes may be bundled or otherwise constrained to sense vibrations from a single location on mechanical system 14. In other cases, various probes of acoustic vibration sensor 16 may be configured to concurrently sense vibrations from multiple locations on mechanical system 14.

Acoustic vibration sensor 16 may include electrical circuitry or electronic processing capability. Such circuitry or processing capability may perform various functions such as analog signal amplification or filtering, digitization, digital signal processing (e.g. transforming or compressing digital signals), and transmission of data in accordance with a data transmission protocol.

Additional sensor 17 may include one or more sensors for sensing one or more properties of mechanical system 14 other than vibrations. For example, additional sensor 17 may include one or more sensors for sensing a temperature of mechanical system 14. As another example, additional sensor 17 may include one or more sensors for sensing another property of mechanical system 14. Such other properties of mechanical system 14 may include, for example, an electrostatic, magnetic, or electromagnetic field; radiation; emitted fumes, particles, droplets, or molecules; or a pressure.

Figure 3:
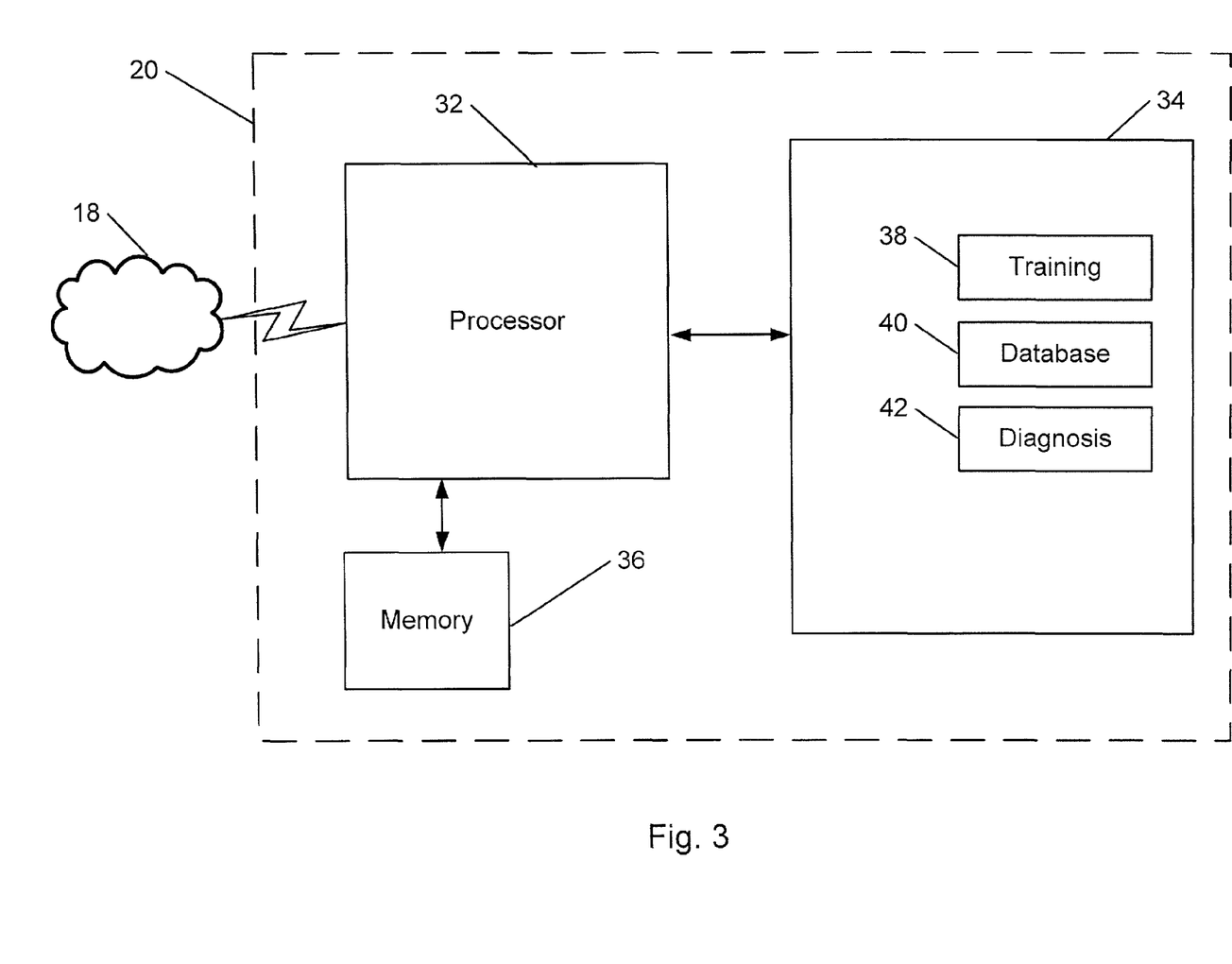
FIG. 3 is a schematic diagram of a server of a system for automatic mechanical system diagnosis, in accordance with an embodiment of the present invention.

Server 20 is configured to communicate via network 18 with portable communications device 12 as well as with any additional portable communications devices 12'. (Each additional portable communications device 12' is configured in a manner similar to, and is configured to function in a manner similar to, portable communications device 12.) Server 20 is configured to process data that is received from portable communications device 12 and, when required, to return a result of the processing to portable communications device 12. (The result may be saved, e.g. in memory 36 or in data storage device 34, for future access, e.g. for the purpose of system management or for tracking a trend.)

FIG. 3 is a schematic diagram of a server of a system for automatic mechanical system diagnosis, in accordance with an embodiment of the present invention.

Server 20 may include a computer or one or more intercommunicating computers. The intercommunicating computers of server 20 may be located at a single location, or may be distributed among several mutually remote locations. Some or all functionality of sever 20 may be provided by a processor 22 of a portable communications device 12 or 12'.

Server 20 includes a processor 32. For example, processor 32 may include one or more processing units, e.g. of one or more computers. Processor 32 may be configured to operate in accordance with programmed instructions stored in memory 36. Processor 32 may be capable of executing an application for automatic diagnosis of a mechanical system.

Processor 32 may communicate with memory 36. Memory 36 may include one or more volatile or nonvolatile memory devices. Memory 36 may be utilized to store, for example, programmed instructions for operation of processor 32, data or parameters for use by processor 32 during operation, or results of operation of processor 32.

Processor 32 may communicate with data storage device 34. Data storage device 34 may include one or more fixed or removable nonvolatile data storage devices. For example, data storage device 34 may include a computer readable medium for storing program instructions for operation of processor 32. Data storage device 34 may be remote from processor 32. In such cases data storage device 34 may be a storage device of a remote server (e.g. of a software provider) a program for automatic diagnosis of a mechanical system in the form of an installation package or packages that can be downloaded and installed for execution by processor 32. Data storage device 34 may be utilized to store data or parameters for use by processor 32 during operation, or results of operation of processor 32.

In particular, data storage device 34 may be utilized to store programmed instructions relating to a training module 38. When operating in a training mode, processor 32 may acquire or obtain vibration-related data and characteristics of a mechanical system from one or more portable communications devices 12 or 12'.

Data that is obtained during operation in a counselor training mode, or data that results from processing of the obtained data, may be stored on data storage device 34 in the form of database 40. Database 40 may include one or more tables. A record or tuple of a table may include one or more of: vibration-related data or one or more parameters that characterize a vibration, data that identifies a mechanical system or a component of a mechanical system, or data that identifies a state of a mechanical system. Data in database 40 may be appropriately indexed or cross-referenced to enable querying database 40 or to enable associating corresponding data in various tables.

Data storage device 34 may be utilized to store programmed instructions relating to a diagnosis module 42. When operating in a diagnosis mode, processor 32 may receive vibration-related data and characteristics of a mechanical system from a portable communications device 12. Processor 32 may query database 40 on the basis of the received data, or otherwise retrieve or obtain data that corresponds to the received data and that indicates a state of the mechanical system. Information related to the state, or related to recommended actions to be performed that relate to the mechanical system, may be prepared for reporting to portable communications device 12.

Processor 32 may communicate with network 18 via a wired or wireless connection.

Processor 32 may be operated to execute a method for automatic diagnosis of a mechanical system, in accordance with an embodiment of the current invention.

Figure 4:
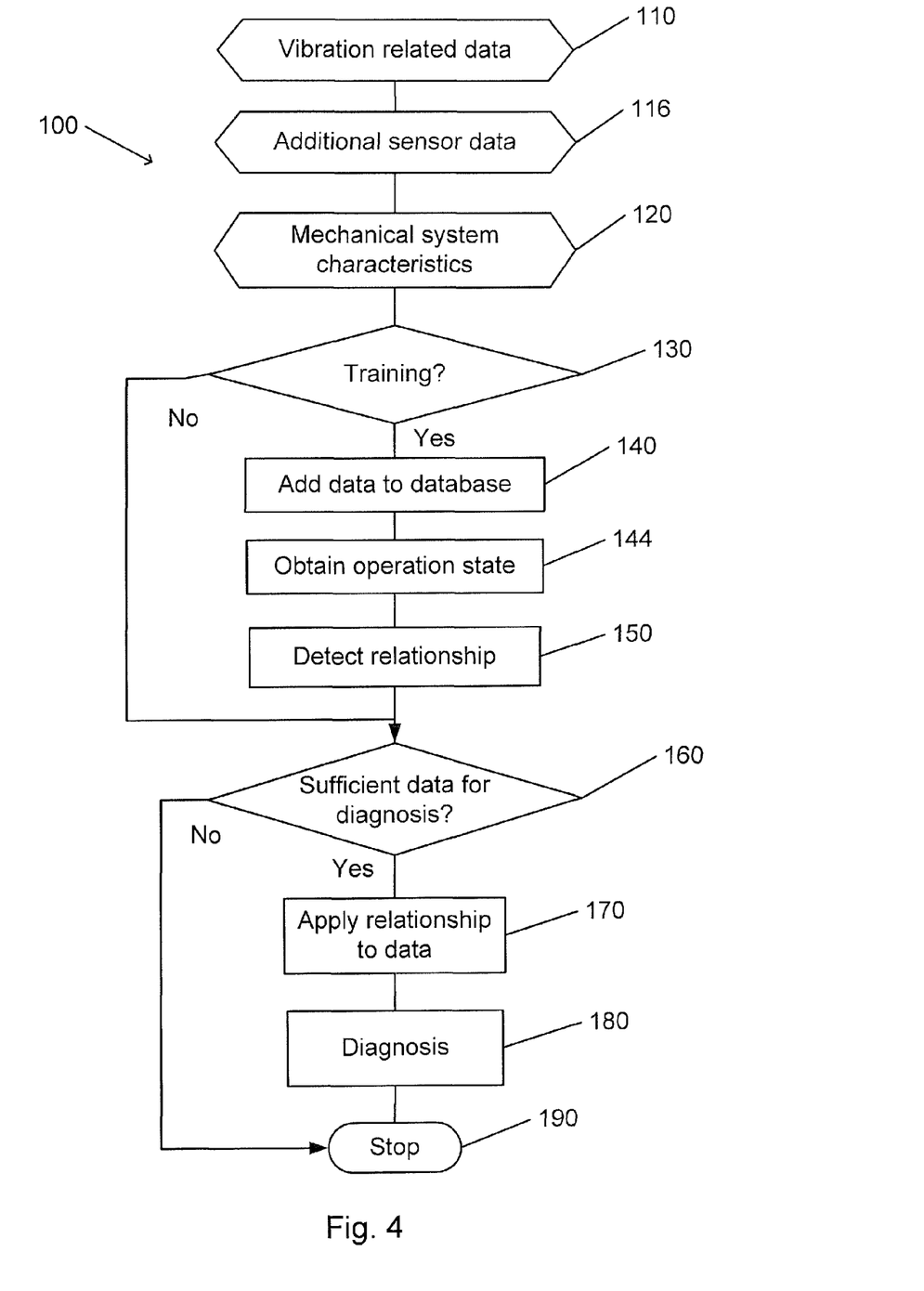
FIG. 4 is a flowchart depicting a method for automatic diagnosis of a mechanical system, in accordance with an embodiment of the current invention.

FIG. 4 is a flowchart depicting a method for automatic diagnosis of a mechanical system, in accordance with an embodiment of the current invention. Automatic diagnosis method 100 may be executed by a processor of a system for automatic diagnosis of a mechanical system. For example, automatic diagnosis method 100 may be executed by a processor of a server of the system for automatic diagnosis of a mechanical system.

Automatic diagnosis method 100 may be executed upon a request or command that is issued by a user (e.g. by operating a control of a portable communications device), or automatically issued by another program or application that is being executed. Automatic diagnosis method 100 may be executed in response to a predetermined event. For example, automatic diagnosis method 100 may be executed when a vibration sensor is attached to, or begins communicating with, a portable communications device, or when vibration-related data is received by the portable communications device.

It should be understood with respect to the flowchart that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of the flowchart has been selected for convenience and clarity only. Operations of the illustrated method may be executed in an alternative order, or concurrently, with equivalent results. Such reordering of operations of the illustrated method should be understood as representing other embodiments of the illustrated method.

In accordance with an embodiments of the present invention, a computer program application stored in a computer-readable medium (e.g., register memory, processor cache, RAM, ROM, hard drive, flash memory, CD ROM, magnetic media, etc.) may include code or executable instructions that when executed may instruct or cause a controller or processor to perform methods discussed herein, such as a method for automatic diagnosis of a mechanical system. The computer-readable medium may be a non-transitory computer-readable media including all forms and types of computer-readable media except for a transitory, propagating signal.

Automatic diagnosis method 100 includes obtaining vibration-related data from a portable communications device (block 110). A vibration of a mechanical system may be sensed by an appropriate vibration sensor, e.g. for a period of a few (e.g. no more than two) seconds. A signal that is generated by the vibration sensor in response to the sensed vibration may be processed (e.g. by an analog or digital processing capability of the vibration sensor or the remote communications device) to yield the vibration-related data. Vibration-related data may include, for example, one or more of a digitized signal that represents a sensed vibration, a compressed signal that represents a sensed vibration, a functional representation of the sensed vibration, a spectrum of the sensed vibration (e.g. frequencies and associated amplitudes), a functional representation of a spectrum of the sensed vibration, a parametric representation of the sensed vibration or its spectrum, or another appropriate representation of a vibration.

Automatic diagnosis method 100 includes obtaining any additional sensed data from a portable communications device (block 116). The additional sensed data may be acquired from a sensor that is configured to sense a property of the mechanical system other than acoustic vibrations. For example, additional sensed data may indicate a temperature of the mechanical system. The temperature may be sensed by an appropriate sensor, e.g. a thermometer or other thermal sensor or probe. A signal that is generated by the additional sensor and that represents a sensed value may be processed (e.g. by an analog or digital processing capability of the additional sensor or the remote communications device) to yield the additional sensed data.

One or more characteristics of the mechanical system may be obtained from the portable communications device (block 120). The characteristics may identify the type of mechanical system (to be understood as including a component of a larger mechanical system).

For example, a user may interact with a user interface via the portable communications device so as to enter information regarding the mechanical system. Entered information may include, for example, a type of machine or component, a model number, a serial number, an indication of a location, a date of manufacture, or other identifying information. The portable communications device or automatic diagnosis system is configured for automatic diagnosis of only one type of mechanical system, or for a limited number of mechanical systems, or only for a previously registered mechanical system. In this case, some or all of the identifying information may be automatically sent, retrieved, or referenced.

As another example, the portable communications device may be used to read an identifying tag, label, or marking. For example, camera of the portable communications device may be pointed at a barcode or matrix barcode, or other identifying marking on the mechanical system or the component. An image analysis capability of the portable communications device or the server may identify a mechanical system on the basis of an imaged shape. A RFID reader of the portable communications device may read an RFID tag on the mechanical system. An NFC The portable communications device may be connected via a suitable connection to a data port of the mechanical system.

The characteristics may indicate a current state of the mechanical system, e.g. with regard to maintenance. For example, the characteristics may include a date of when a previous maintenance action was performed on the mechanical system, or a nature of the maintenance action. The characteristics may include data related to operation of the mechanical system concurrent with the sensed vibrations. Such data may include, for example, a speed of the mechanical system (e.g. of revolution of a component or a linear speed of a component), a force exerted, a load, a flow rate, a compression, a type of fluid or load being transported, a state of a control or valve, an internal temperature or pressure, a combustion rate, electrical power consumption, relevant environmental conditions (e.g. temperature, humidity, atmospheric components), or other relevant data.

The automatic diagnosis system may be operating in a training mode (block 130). When in a training mode, the automatic diagnosis system accumulates data to enable correlating a vibration of the mechanical system with a state of operation of the system. A training mode may relate to a particular mechanical system. For example, the automatic diagnosis system may be in a training mode with respect to one type of mechanical system, and not with respect to another.

A user of the mechanical system may be requested (e.g. via an output device of the portable communications device) to acquire periodically (e.g. every few days or weeks) vibration-related data (block 110), additional sensed data (block 116), and any relevant mechanical system characteristics (block 120). The obtained data is stored in a database or other storage mode that enables retrieval when required (block 140).

When in a training mode, data related to an operation state of the mechanical system may be obtained (block 144). For example, when maintenance or repair operations are performed on the mechanical system, data that defines the maintenance or repair operations may be obtained. Data that defines a malfunction or breakdown of the mechanical system may be obtained. For example, a knowledgeable user (e.g. maintenance or repair personnel) may interact with a user interface (e.g. of the portable communications device, of the server, or of another device that enables communication between the user and the server) to enter the operational state data. As another example, a user may operate a camera of the portable communications device to acquire an image of an invoice, itemized bill, or other printed or written indication of the operational state. The acquired image may be interpreted (e.g. using image processing or optical character recognition techniques) to extract the operational state data.

Acquired vibration-related data and additional sensed data from a period that preceded obtaining the operational state data may be analyzed to detect a relevant pattern or relationship (block 150). For example, a vibration at a particular vibration frequency may be detected as becoming more or less intense (e.g. greater or smaller amplitude) relative to a vibration with another vibration frequency in a period that preceded a malfunction or repair. A relationship may be saved for application to obtained vibration-related data (and additional sensed data) for a particular mechanical system or family of mechanical systems. A saved relationship may be represented in the form of a lookup table (e.g. relating relative amplitude to estimated time of repair or type of repair), in a functional form, or other form that indicates a connection between vibration-related data (and any additional sensed data, e.g. temperature) and a state of operation.

Detecting a relationship may include fitting a model to the data in the database. Appropriate statistical techniques may be applied in order to fit the model to the data. For example, if a model includes a functional relationship, an appropriate least-squares fit or similar technique may be applied.

If insufficient data has been obtained, no pattern or relationship may be detected. Alternatively, a relationship may be detected, but a confidence in the relationship may be low. A confidence value that is associated with the detected relationship may indicate a degree of confidence in a relationship. As more training data is acquired, the confidence in the relationship may increase.

Sufficient data may exist, e.g. in a database or other form, to enable generation of a diagnosis of the mechanical system based on the obtained vibration-related data and on any additional sensed data (block 160). For example, when vibration-related data is obtained for a particular mechanical system (e.g. as indicated by obtained mechanical system characteristics), a processor that is executing automatic diagnosis method 100 may check the database for a pattern or relationship that relates to that mechanical system. Detection of an appropriate relationship, an indicated confidence level that exceeds a threshold value, or another indicator, such as a flag, that indicates that sufficient data exists may be interpreted as indicating that sufficient data exists.

If insufficient data exists for a diagnosis, execution of automatic diagnosis method 100 ends (block 190).

A detected relationship may be applied to the obtained vibration-related data (block 170). For example, vibration-related data and any additional sensed data may be used to select an appropriate entry in a lookup table that represents the relationship, may be input as an argument to a functional relationship that represents the relationship, or otherwise compared to the detected relationship. Application of the relationship may give a current state of operation or other data that may be utilized to generate a diagnosis of the mechanical system. Where appropriate (e.g. where the state of operation is expressed numerically as a quantity, e.g. mean time to failure), values may be interpolated to yield a current state of operation of the mechanical system.

Application of the relationship to the vibration-related data may yield a diagnosis for the mechanical system (block 180). A diagnosis may indicate a state of operation of the mechanical system, a prediction of future operation of the mechanical system (prognosis), a recommendation for maintenance or monitoring actions, or any combination of these. For example, a diagnosis may indicate a mean time to failure of the mechanical system, an indication of a faulty component of the mechanical system, an indication of an operation parameter that may be changed to improve operation of the mechanical system, an indication of a maintenance operation to be performed in order to reduce a chance of failure of the mechanical system, or another indication of a current operational state of the mechanical system.

The diagnosis is reported to the portable communications device. The portable communications device may display or otherwise output the reported diagnosis such that a user of the portable communications device may receive the diagnosis. The reported diagnosis may include a recommended maintenance operation to be performed on the mechanical system, an estimated time to failure in the absence of the performance of the recommended maintenance operation, an indication of a level of confidence in the diagnosis, an indication of a general state of operation of the mechanical system (e.g. good versus bad, or a numerical or graphical indicator), or another output related to a current or predicted operational state of the mechanical system.

The diagnosis may be saved or stored for future access. For example, the diagnosis (or related data) may be stored on a storage device that is in communication with the server, the portable communications device, or with another device that is a component of or is in communication with the automatic diagnosis system. The stored diagnosis may thus be accessible at a later time to a user (e.g. a subscriber to the automatic diagnosis system) that has access to an output device of the server, of the portable communications device, or of another device with access to the automatic diagnosis system.

The invention claimed is:

1. A system for maintenance of at least one mechanical machine having at least one shared mechanical characteristic with a plurality of mechanical machines, the system comprising:

a plurality of operational parameter sensors coupled to a corresponding plurality of mechanical machines having at least one shared mechanical characteristic for sensing at least one operational parameter thereof, said plurality of operational parameter sensors coupled to said corresponding plurality of mechanical machines providing output indications of associated operational parameters of said corresponding plurality of mechanical machines; and a computer comprising a processor, a memory and a non-transitory, tangible computer-readable medium in which computer program instructions are stored, which instructions, when read by said computer, cause the computer to provide the following functionalities:

receiving said output indications of associated operational parameters of said corresponding plurality of mechanical machines;

accumulating said output indications of said associated operational parameters of said corresponding plurality of mechanical machines and providing accumulated associated operational parameters;

providing an output indication of a historical correlation between said associated operational parameters of said plurality of mechanical machines based on analyzing said accumulated associated operational parameters;

receiving said output indication of said historical correlation between said associated operational parameters of said plurality of mechanical machines;

providing a human sensible output alarm indication including at least a prediction of failure of at least one given mechanical machine having said at least one shared mechanical characteristic, based on applying said historical correlation between said associated operational parameters of said plurality of mechanical machines to output indications of said at least one operational parameter of said at least one given mechanical machine sensed by a corresponding one of said plurality of operational parameter sensors; and scheduling at least one maintenance related operation based on said human sensible output alarm indication.

2. A system for maintenance of at least one mechanical machine according to claim 1 and wherein said plurality of operational parameter sensors includes a vibration sensor.

3. A system for maintenance of at least one mechanical machine according to claim 1 and wherein said given mechanical machine is one of said plurality of mechanical machines.

4. A system for maintenance of at least one mechanical machine according to claim 1 and wherein said given mechanical machine is not one of said plurality of mechanical machines.

5. A system for maintenance of at least one mechanical machine according to claim 1 and wherein said human sensible output alarm indication is based on a current operational parameter output of said given mechanical machine as sensed by one of said plurality of operational parameter sensors.

6. A system for maintenance of at least one mechanical machine according to claim 1 and wherein said human sensible output alarm indication includes a mean time between failures (MTBF) indication.

7. A system for maintenance of at least one mechanical machine according to claim 1 and wherein said human sensible output alarm indication includes a confidence metric indication indicating the reliability of said prediction.

8. A system for maintenance of at least one mechanical machine according to claim 1 and wherein said human sensible output alarm indication includes a recommendation for at least one of a repair operation and a maintenance operation.

9. A method for scheduling maintenance of at least one mechanical machine having at least one shared mechanical characteristic with a plurality of mechanical machines, the method comprising:

coupling a plurality of operational parameter sensors to a corresponding plurality of mechanical machines having at least one shared mechanical characteristic for sensing at least one operational parameter thereof, said plurality of operational parameter sensors providing output indications of associated operational parameters of said corresponding plurality of mechanical machines; and receiving, by a computer including a processor and a memory, said output indications of associated operational parameters of said corresponding plurality of mechanical machines;

accumulating, utilizing said computer, said output indications of said associated operational parameters of said corresponding plurality of mechanical machines and providing accumulated associated operational parameters;

providing, utilizing said computer, an output indication of a historical correlation between said associated operational parameters of said corresponding plurality of mechanical machines based on analyzing said accumulated associated operational parameters;

receiving said output indication of said historical correlation between associated operational parameters of said corresponding plurality of mechanical machines;

applying said historical correlation between said associated operational parameters to output indications of said at least one operational parameter of at least one given machine, sensed by a corresponding one of said plurality of operational parameter sensors;

providing at least one maintenance related operation human sensible output indication, including at least a prediction of failure of said at least one mechanical machine having said at least one shared mechanical characteristic, based on said applying said historical correlation; and scheduling at least one maintenance related operation based on said at least one maintenance related operation human sensible output indication.

10. A method for scheduling maintenance of at least one mechanical machine according to claim 9 and wherein said plurality of operational parameter sensors includes a vibration sensor.

11. A method for scheduling maintenance of at least one mechanical machine according to claim 9 and wherein said given mechanical machine is one of said plurality of mechanical machines.

12. A method for scheduling maintenance of at least one mechanical machine according to claim 9 and wherein said given mechanical machine is not one of said plurality of mechanical machines.

13. A method for scheduling maintenance of at least one mechanical machine according to claim 9 and wherein said at least one maintenance related operation human sensible output indication is based on a current operational parameter output of said given mechanical machine as sensed by one of said plurality of operational parameter sensors.

14. A method for scheduling maintenance of at least one mechanical machine according to claim 9 and wherein said at least one maintenance related operation human sensible output indication includes a mean time between failures (MTBF) indication.

15. A method for scheduling maintenance of at least one mechanical machine according to claim 9 and wherein said at least one maintenance related operation human sensible output indication includes a confidence metric indication indicating the reliability of said prediction.

* * * * *